(12) United States Patent
Meloni

(10) Patent No.: US 6,466,642 B1
(45) Date of Patent: Oct. 15, 2002

(54) METHODS AND APPARATUS FOR THE IN-SITU MEASUREMENT OF CMP PROCESS ENDPOINT

(75) Inventor: Mark A. Meloni, Tempe, AZ (US)

(73) Assignee: SpeedFam-IPEC Corporation, Chandler, AZ (US)

(*) Notice: Subject to any disclaimer, the term of this patent is extended or adjusted under 35 U.S.C. 154(b) by 6 days.

(21) Appl. No.: 09/586,934

(22) Filed: Jun. 2, 2000

(51) Int. Cl.⁷ .............................................. G01N 23/223

(52) U.S. Cl. .......................................... 378/44; 378/50

(58) Field of Search .......................... 378/44, 45, 46, 378/50, 70, 79, 86, 88, 89

(56) References Cited

U.S. PATENT DOCUMENTS

| | | | |
|---|---|---|---|
| 4,959,848 A | * | 9/1990 | Parobek ..................... 378/46 |
| 5,483,568 A | * | 1/1996 | Yano et al. ................. 378/44 |
| 5,740,226 A | | 4/1998 | Komiya et al. |

OTHER PUBLICATIONS

"Multilayer Film Thickness Measurement", Axic Application Report No. 5, 1992, pp. 1–2.

"The Principle of X–ray Fluorescence Analysis in Thin Film Process Control", Axic Application Report No. 6, 1993, pp. 1–4.

"A Production Line Thin Film Composition and Thickness Monitor", Precision 1000–B Brochure, 1998, 2 sides.

* cited by examiner

Primary Examiner—David P. Porta
(74) Attorney, Agent, or Firm—Snell & Wilmer LLP

(57) ABSTRACT

A method and apparatus for the in-process measurement of the thickness and composition of a material layer on a workpiece during chemical mechanical polishing are disclosed. The chemical mechanical polishing apparatus includes a platen having a polishing pad mounted thereto and an x-ray probe assembly mounted into a recessed volume in the platen. The x-ray probe assembly includes an x-ray emitter and an x-ray detector. The thickness and composition of the material layer on the workpiece is measured by generating and directing an incident x-ray beam onto a location on the surface of the wbrkpiece, and then capturing the resultant fluorescent beam and processing data from the resultant fluorescent beam.

15 Claims, 4 Drawing Sheets

METHODS AND APPARATUS FOR THE IN-SITU MEASUREMENT OF CMP PROCESS ENDPOINT

BACKGROUND

1. Field of the Invention

The present invention generally relates to methods and apparatus for measuring the chemical mechanical polishing (CMP) process endpoint on a semiconductor wafer during the planarization process, and more particularly, to methods and apparatus for generating an X-ray beam and directing the beam onto the surface of the workpiece to be measured, and analyzing the reflection of the X-ray beam to obtain real-time CMP endpoint (i.e., process endpoint) information.

2. Description of the Related Art

The production of semiconductor devices begins with the creation of high quality semiconductor wafers. Because of the high precision required in the production of these semiconductor devices, an extremely flat surface is generally needed on at least one side of the semiconductor wafer to ensure proper accuracy and performance of the microelectronic structures being created on the wafer surface. CMP is often used to remove material from the surface of the wafer to provide a relatively flat surface.

Such polishing is well known in the art and generally includes placing one side of the wafer in contact against a flat polishing surface, and moving the wafer and the polishing surface relative to each other. A slurry, including abrasive particles and/or chemicals that react with the material on the wafer surface to dissolve the material, may also be placed in contact with the wafer surface to assist in removing a portion of the material. During the polishing or planarization process, the wafer is typically pressed against the polishing pad while the pad rotates. In addition, to improve the polishing effectiveness, the wafer may also rotate and oscillate back and forth over the surface of the polishing pad.

A well prepared polishing pad facilitates the uniform, high precision planarization of wafers. This is particularly important when polishing down the material layer on a semiconductor wafer during the manufacture of semiconductor devices.

Presently known methods for measuring the thickness of a material layer on a semiconductor wafer involve measuring the total thickness of an applied material layer, determining the desired thickness of the material layer after planarization, calculating the pressure to be applied during the polishing or planarization process, and further calculating the approximate time required to remove a predetermined amount of material layer for a given pressure and slurry combination. Once the desired removal rate (often expressed in nanometers per minute) is ascertained, a statistical inference is employed to determine the approximate amount of time necessary to remove a desired amount of material. After the wafers have undergone planarization for an amount of time calculated to remove a desired thickness of the material layer, the wafers or workpieces are removed from the machine and the actual thickness of the material layer is measured off-line, for example, through the use of laser interferometric techniques. If it is determined that the material layer is still too thick after initial planarization, the workpieces must be reinstalled onto the CMP machine for further material layer removal. If, on the other hand, an excessive amount of material layer has been removed, it may be necessary to scrap the wafers, resulting in substantial unnecessary costs.

In general, visible light is not able to sense changes in thickness of the material layer, unless the layer is less than approximately 600 Angstroms thick. Ultraviolet light and x-ray beams can penetrate these material layers when they are greater than 600 Angstroms thick. Specifically, x-ray techniques, as used in well known x-ray fluorescence (XRF) measurement systems, can effectively and non-destructively measure the thickness and composition of the material layer once the wafer is removed from the CMP machine. However, this technique has not been utilized in-situ in conjunction with a CMP machine during the planarization or polishing of the wafer for real-time measurement of the thickness of the material layer on the surface of a wafer.

An apparatus is thus needed which accurately measures the material layer thickness (and particularly the CMP process endpoint) during the CMP process (in-situ) to overcome the shortcomings of the prior art.

SUMMARY OF THE INVENTION

The present invention provides an improved method and apparatus for measuring the chemical mechanical polishing (CNIP) process endpoint on a workpiece during the planarization process. More particularly, the present invention provides a device to measure the thickness of a material layer on the surface of the workpiece by generating an x-ray beam, directing the beam onto the surface of the workpiece, and analyzing the resultant fluorescent beam to obtain real-time CMP endpoint information including the thickness of the material layer.

In accordance with an exemplary embodiment of the present invention, an x-ray probe assembly is mounted onto a CMP machine. The x-ray probe assembly comprises an x-ray emitter, an x-ray detector, and suitable x-ray optics as required including collimators and lenses. The x-ray emitter is configured to generate and direct an incident x-ray beam onto a location on the surface of the workpiece as the workpiece is being polished. The incident x-ray beam is scattered from and absorbed into the surface of the workpiece and a resultant fluorescent beam is produced. The x-ray detector is configured to receive the resultant fluorescent beam, and the resultant fluorescent beam is then processed by a processor to determine the thickness and composition of the material layer or layers at the incident location on the surface of the workpiece.

BRIEF DESCRIPTION OF THE DRAWINGS

A more complete understanding of the present invention may be derived by referring to the detailed description and claims when considered in connection with the following illustrative Figures, which may not be to scale. In the following Figures, like reference numbers refer to similar elements throughout the Figures.

DETAILED DESCRIPTION

The present invention relates to a method and apparatus used in conjunction with a chemical mechanical polishing (CMP) machine, for the in-process thickness and composition measurement of one or more material layers on a workpiece using a short wavelength light probe. Although the present invention may be used in conjunction with the polishing of a variety of workpieces such as computer disks, optical disks and the like, the present invention is conveniently described below in connection with the polishing of semiconductor wafers.

Figure 1:
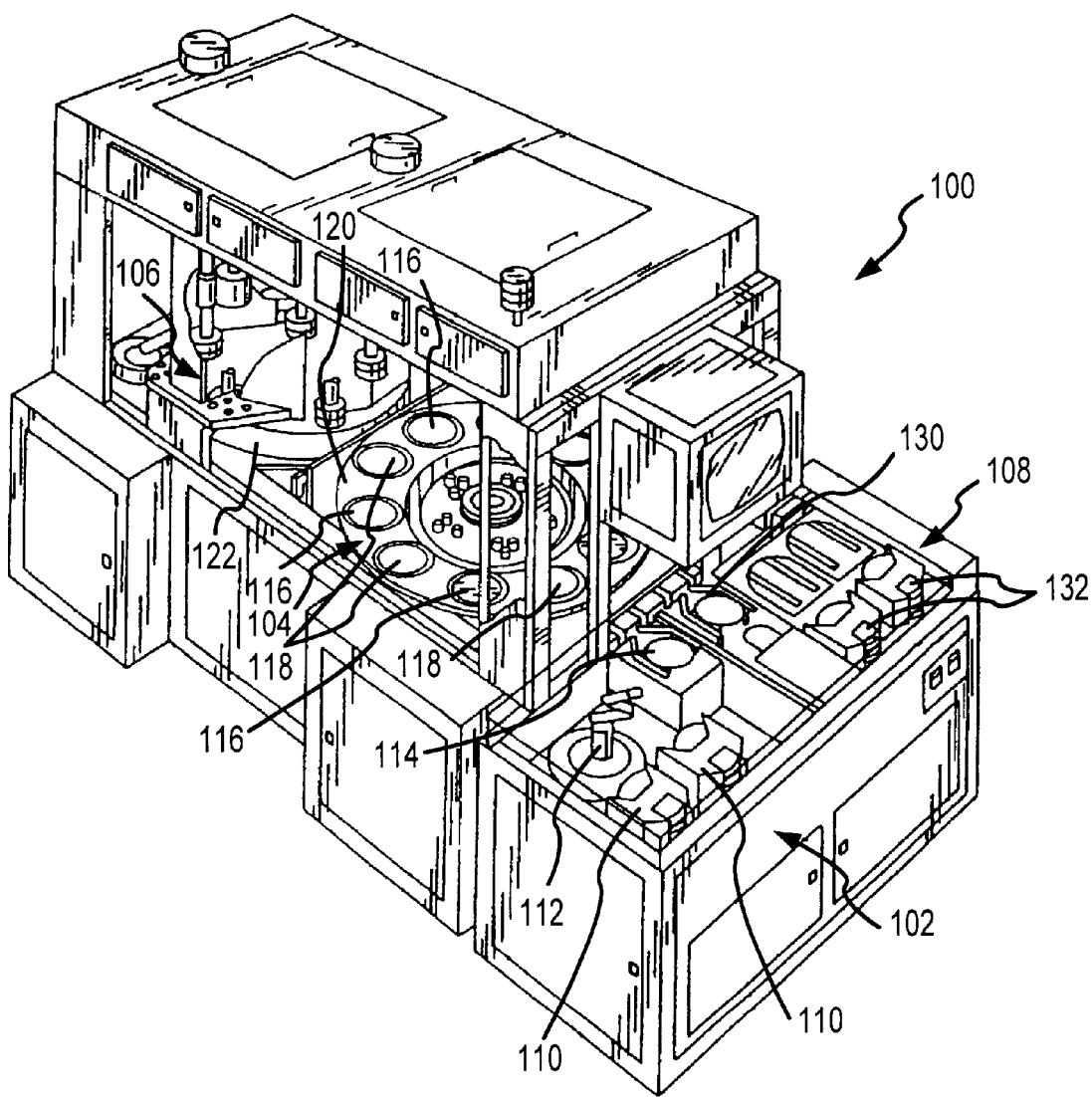
FIG. 1 illustrates, in perspective view, an exemplary CMP machine useful in the context of the present invention.
Figure 2:
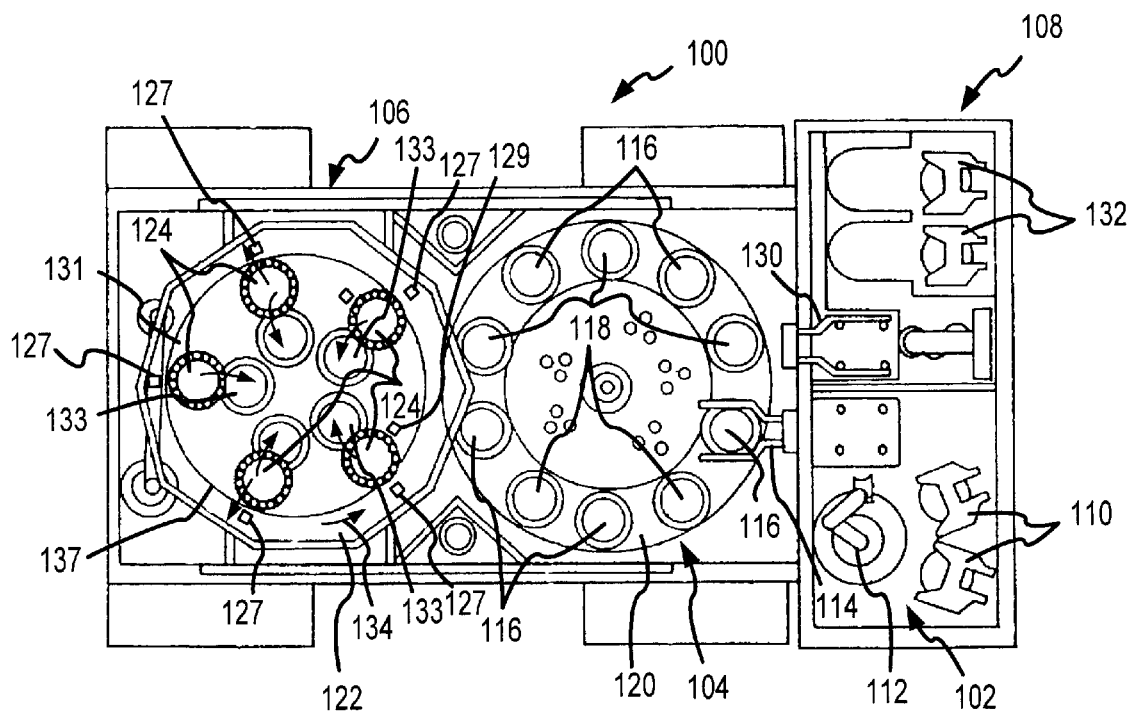
FIG. 2 illustrates, in top view, the CMP machine of FIG. 1, showing an exemplary orientation of an x-ray probe assembly in accordance with the present invention.

Referring to FIGS. 1 and 2, a CMP machine 100 is illustrated in accordance with an exemplary embodiment of the present invention. CMP machine 100 suitably comprises a multiple head wafer polishing machine which accepts wafers which have been loaded into wafer cassettes 110, polishes and rinses the wafers, and reloads the wafers back into wafer cassettes 110 for subsequent processing. CMP machine 100 typically includes an unload station 102, a wafer transition station 104, a polishing station 106, and a wafer rinse and load station 108.

In operation, cassettes 110, each holding a plurality of wafers, are loaded into CMP machine 100 at unload station 102. Next, a robotic wafer carrier arm 112 removes the wafers from cassettes 110 and places them, one at a time, on a first wafer transfer arm 114. Wafer transfer arm 114 then sequentially lifts and moves each wafer into wafer transition station 104. That is, transfer arm 114 suitably places an individual wafer on one of a plurality of wafer pick-up stations 116 which reside on a rotatable table 120 within wafer transition station 104. Rotatable table 120 also suitably includes a plurality of wafer drop-off stations 118 which alternate with pick-up stations 116. After a wafer is deposited on one of the plurality of pick-up stations 116, table 120 rotates so that a new station 116 aligns with transfer arm 114. Transfer arm 114 then places the next wafer on the new empty pick-up station 116. This process continues until all pick-up stations 116 are filled with wafers. In ID the illustrated embodiment of the invention, table 120 includes five pick-up stations 116 and five drop-off stations 118.

Next, a wafer carrier apparatus 122, comprising individual wafer carrier elements 124, suitably aligns itself over table 120 so that respective carrier elements 124 are positioned directly above the wafers which reside in respective pick-up stations 116. The carrier apparatus 122 then drops down and picks up the wafers from their respective stations and moves the wafers laterally such that the wafers are positioned above polishing station 106. Once above polishing station 106, carrier apparatus 122 suitably lowers the wafers, which are held by individual elements 124, into operative engagement with a polishing pad 131 which sits atop a platen 137. During operation, platen 137 causes polishing pad 131 to rotate about its vertical axis (substantially along arrow 134). At the same time, individual carrier elements 124 spin the wafers about their respective vertical axes and oscillate the wafers back and forth across pad 131 (substantially along arrow 133) as the wafers press against polishing pad 131. In this manner, material is removed from a surface of the wafer by polishing or planarization. Such polishing often occurs in the presence of a slurry composition deposited between the wafer and the polishing pad.

After an appropriate period of time, the wafers are removed from polishing pad 131, and carrier apparatus 122 transfers the wafers back to transition station 104. Carrier apparatus 122 then lowers individual carrier elements 124 and deposits the wafers onto drop-off stations 118. The wafers are then removed from drop-off stations 118 by a second transfer arm 130. Transfer arm 130 suitably lifts each wafer out of transition station 104 and transfers them into wafer rinse and load station 108. In the load station 108, transfer arm 130 holds the wafers while they are rinsed. After a thorough rinsing, the wafers are reloaded into cassettes 132 for further processing or packaging.

As shown in FIG. 2, a recessed volume 127 is suitably formed within platen 137 at a position so that carrier element 124 passes over recessed volume 127 as platen 137 and carrier element 124 move relative to each other. Recessed volume 127 is preferably located at a position along the top surface of platen 137 that is approximately one-half of the platen radius from the center of platen 137. However, it will be appreciated that recessed volume 127 may be positioned at other positions within platen 137 that would facilitate measuring wafer carrier element 124 as described below.

Figure 3:
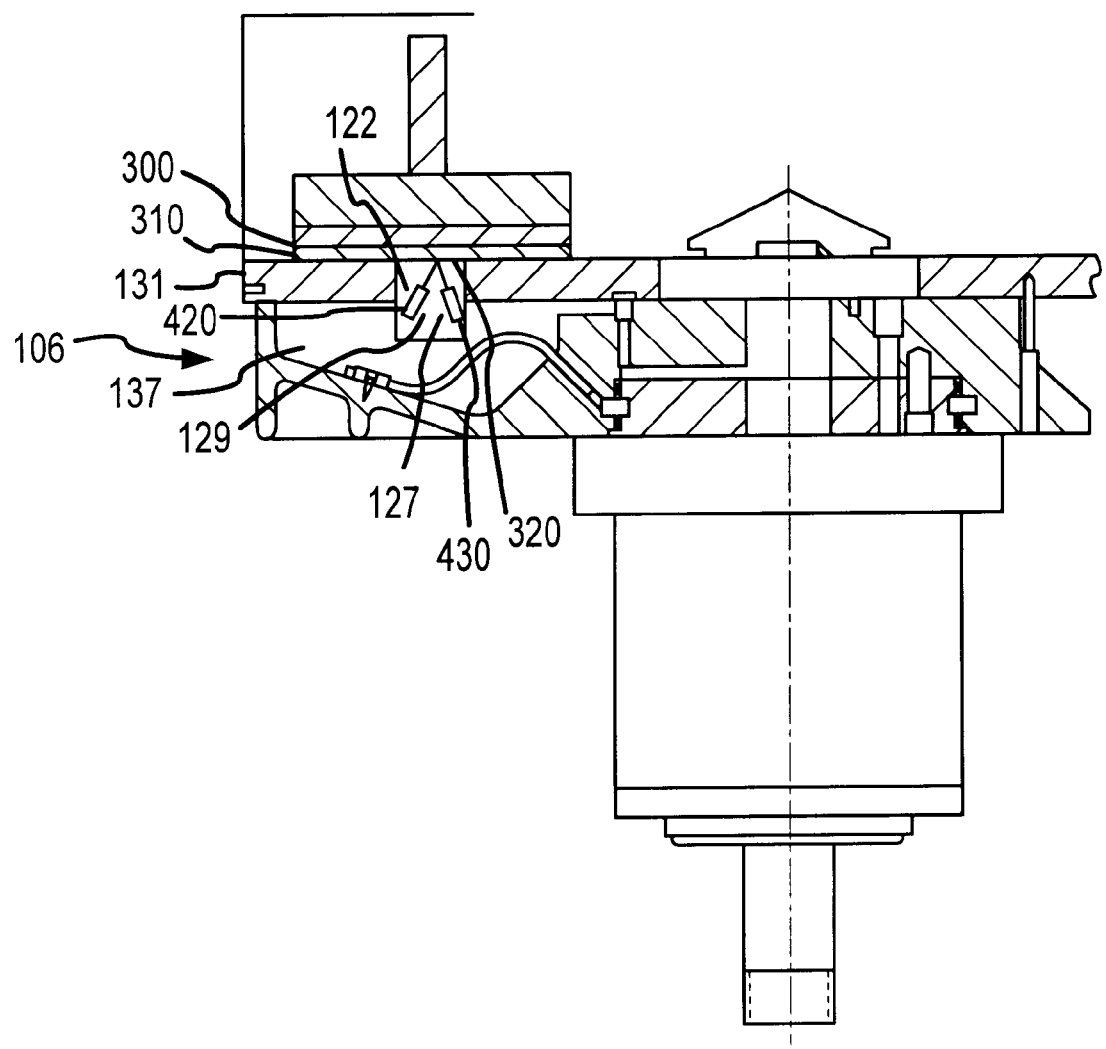
FIG. 3 illustrates, in cross section, a portion of a polishing station in accordance with the present invention.

FIG. 3 illustrates a portion of polishing station 106 in greater detail showing recessed volume 127 and platen 137. Polishing station 106 is suitably configured to remove material from a lower surface 310 of wafer 300. As described above, wafer 300 is pressed against the polishing pad of platen 137 while wafer 300 is rotated relative to polishing pad 131 while at least a portion of surface 310 is in contact with at least a portion of polishing pad 131. An x-ray probe assembly 129 is located in recessed volume 127 such that x-ray probe assembly 129 is below the top surface of platen 137.

Figure 4:
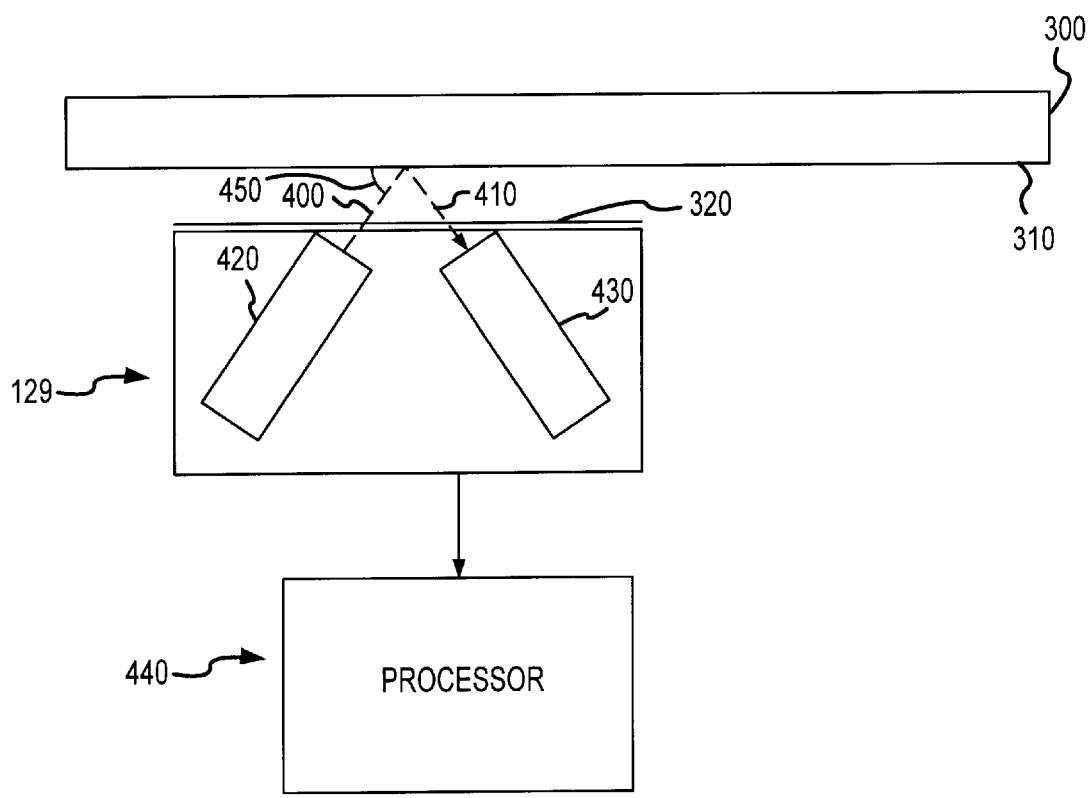
FIG. 4 illustrates, in schematic view, the configuration of the probe assembly of FIG. 2 with a wafer in, the field of view, of the probe.

As shown in FIG. 4, x-ray probe assembly 129, in accordance with an exemplary embodiment of the present invention, suitably comprises an x-ray emitter 420 and an x-ray detector 430. X-ray emitter 420 may be a conventional x-ray emitting tube (e.g., deuterium lamp) producing x-rays at wavelengths of 0.01 Angstroms to 100 Angstroms. An example of a suitable x-ray detector is the XR-1 00CR detector from Amptek, Inc. of Bedford, Mass.

Referring back to FIG. 3, X-ray probe assembly 129 is preferably rigidly mounted into recessed volume 127 such that detector 430 and emitter 420 are directed at equal angles relative to wafer surface 310. This angle may range from 0 to 90 degrees, but is preferably between 40 to 60 degrees. To contain recessed volume 127 and to isolate x-ray assembly 129 from processing fluids and other environmental factors, a window 320 may be located between x-ray assembly 129 and wafer 300. Window 320 may comprise any material that allows the transport of x-rays, but window 320 preferably comprises polymers, glasses such as $M_gF_2$, or metals known to transport x-rays such as beryllium. Similarly, an open aperture may be used in the polishing pad. to increase x-ray transport intensity to wafer 300 and reduce unnecessary scattering. As the polishing pad is made of a thin polymer material, an aperture is not required.

X-ray emitter 420 is configured to direct an x-ray beam 400 onto a location on surface 310 of wafer 300 as the wafer is being polished. As indicated above and illustrated in FIG. 4, x-ray emitter 420 is angled to point at wafer 300 so that angle 450 between incident x-ray beam 400 and wafer 300 is preferably in the range of 40 to, 60 degrees. X-ray detector 430 is configured to receive a resultant fluorescent beam 410 that results from x-ray beam 400 being absorbed, scattered, and interfering within wafer 300, and then resultant x-ray beam 410 being emitted from the wafer. The intensity of resultant fluorescent beam 410 is dependent upon the thickness and composition of the material layer on wafer 300. Thus, the intensity of the resultant fluorescent beam may be processed by processor 440, coupled to x-ray probe assembly 127, in order to determine the thickness and composition of the material layer at the location where x-ray beam 400 was incident to the surface of wafer 300. Processor 440 is preferably coupled to a display device or a printer so that human readable output of the thickness and composition of the material layer is obtained.

In accordance with an exemplary embodiment of the present invention, x-ray probe assembly 127 uses commonly known x-ray fluorescence (XRF) measurement technology in order to gather x-ray data for the real-time measurement of CMP endpoint processing, including the measurement properties such as the material layer thickness and composition on surface 310 of wafer 300. For a discussion of XRF technology, see, for example, AXIC Application Report 5, Multilayer Film Thickness Measurement, available from AXIC Inc., Santa Clara, Calif. As is well known in the art, XRF measurement systems include detectors utilizing a Wavelength Dispersive Spectrometer (WDS) or an Energy Dispersive Spectrometer (EDS). Generally, a WDS system will give a higher precision measurement than an EDS system. However, for some applications, an EDS system may be preferred in order to optimize analysis time.

A typical property to be measured, such as the material layer thickness on surface 310 of wafer 300, can be determined by processing resultant fluorescent beam 410 in the following manner. Surface 310 is comprised of a known material that has a characteristic x-ray spectrum. Similarly, the target material used in x-ray emitter 420 to generate x-ray beam 400 has characteristic x-rays that are also known. Thus, incident x-ray beam 400 has a known wavelength. The absorption cross sections for x-rays of known wavelengths in a known material have been extensively measured. The total absorption of x-ray beam 400 into the known material of surface 310 is a function of the thickness of the material. Thus, the intensity of resultant fluorescent beam 410 can be processed to determine the thickness of the material.

The present invention has been described above with reference to an exemplary embodiment. However, those skilled in the art will recognize that changes and modifications may be made to the exemplary embodiment without departing from the scope of the present invention. For example, the various components and processing steps of the methods and apparatus for the in-process or in-situ measurement of CMP process endpoint may be implemented in alternate ways depending upon the particular application or in consideration of any number of cost functions associated with the operation of the system, e.g., the x-ray emitter and detector may be positioned separately in different recessed volumes. In addition, the techniques described herein may be extended or modified for use with various other applications. These and other changes or modifications are intended to be included within the scope of the present invention.

What is claimed is:

1. A chemical mechanical polishing apparatus configured to measure properties of a material layer on a workpiece during polishing of the workpiece, the apparatus comprising:

a rotatable platen having an upper surface;

a polishing pad mounted on the upper surface of the platen;

an x-ray probe assembly, disposed proximate the platen, comprising:

an x-ray emitter configured to generate and direct an incident x-ray beam onto a location on a surface of the workpiece as the workpiece is being polished on the polishing pad, wherefrom in response to the incident x-ray beam, a resultant fluorescent beam is produced; and an x-ray detector configured to receive the resultant fluorescent beam, wherein the resultant fluorescent beam is processed, wherein the resultant fluorescent beam is processed to determine the properties of the material layer at the location on the surface of the workpiece.

2. The apparatus of claim 1, wherein the x-ray probe assembly is mounted into a recessed volume in the platen.

3. The apparatus of claim 1, wherein the workpiece comprises a semiconductor wafer.

4. The apparatus of claim 1, wherein one of the properties is a thickness of the material layer.

5. The apparatus of claim 1, wherein one of the properties is a composition of the material layer.

6. The apparatus of claim 1 further comprising a window disposed between the x-ray probe assembly and the surface of the workpiece, wherein the window is configured to facilitate travel of the x-ray beam from the x-ray emitter to the workpiece and facilitate travel of the resultant fluorescent beam from the workpiece to the x-ray detector.

7. The apparatus of claim 1, wherein the resultant fluorescent beam comprises an x-ray fluorescence signal.

8. The apparatus of claim 1, wherein the x-ray emitter is directed at the location on the surface of the workpiece at an angle in the range of 40 to 60 degrees.

9. A method for measuring properties of a material layer on a workpiece during polishing of a surface of the workpiece, comprising the steps of:

pressing the workpiece against a surface of a rotating polishing pad mounted on a platen such that the workpiece is polished by the rotating polishing pad;

disposing an x-ray probe assembly proximate the platen;

generating and directing an x-ray beam onto a location on the surface of the workpiece, wherein in response to the x-ray beam a resultant fluorescent beam is produced; and receiving the resultant fluorescent beam from the surface of the workpiece, wherein the resultant fluorescent beam provides information related to the properties.

10. The method according to claim 9, wherein the workpiece comprises a semiconductor wafer.

11. The method according to claim 9, wherein the resultant fluorescent beam comprises an x-ray fluorescence signal.

12. The method according to claim 9, wherein the generating and directing step further comprises directing the x-ray emitter at the location on the surface of the workpiece at an angle in the range of 40 to 60 degrees.

13. The method according to claim 9 further including the step of processing the resultant fluorescent beam to determine the properties of the material layer at the location on the surface of the workpiece.

14. The method according to claim 13, wherein one of the properties is a thickness of the material layer.

15. The method according to claim 13, wherein one of the properties is a composition of the material layer.

* * * * *